United States Patent [19]
Reichle et al.

[11] Patent Number: 5,852,146
[45] Date of Patent: *Dec. 22, 1998

[54] CATALYST FOR THE PRODUCTION OF OLEFIN POLYMERS

[75] Inventors: Walter Thomas Reichle, Warren; Frederick John Karol, Belle Mead, both of N.J.

[73] Assignee: Union Carbide Chemicals & Plastics Technology Corporation, Danbury, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 670,507

[22] Filed: Jun. 27, 1996

[51] Int. Cl.$^6$ ....................................................... C08F 4/64
[52] U.S. Cl. .......................... 526/172; 526/161; 526/901; 546/6; 546/7; 502/102; 502/103; 502/117; 502/150
[58] Field of Search ............................ 546/6, 7; 502/102, 502/103, 117, 150; 526/161, 172, 901

[56] References Cited

U.S. PATENT DOCUMENTS

| | | | |
|---|---|---|---|
| 1,607,196 | 11/1926 | Hahl et al. | 546/7 |
| 3,900,452 | 8/1975 | Valvassori | 260/80.78 |
| 4,652,647 | 3/1987 | Schlosberg et al. | 546/7 |
| 5,280,000 | 1/1994 | Kakugo et al. | 502/121 |
| 5,552,547 | 9/1996 | Shi | 546/7 |
| 5,637,660 | 6/1997 | Nagy et al. | 526/160 |

FOREIGN PATENT DOCUMENTS

| | | |
|---|---|---|
| 45-024 589 B | of 1970 | Japan . |
| 45-038 069 B | of 1970 | Japan . |
| 1 049 091 | 11/1966 | United Kingdom . |
| WO 91 10634 A | 7/1991 | WIPO . |
| WO 93 02087 A | 2/1993 | WIPO . |
| WO 96 33202 A | 10/1996 | WIPO . |

OTHER PUBLICATIONS

M.J. Frazer et al., "Reactions of 8–quinolinol with Covalent Halides. Part I. Tin and Titanium Tetrachlorides." Journal of Chemical Society No. 6, 1966, London (UK), pp. 544–549.
M.J. Frazer et al., "Reactions of 8–Quinolinol with Covalent Halides. Part II. Tin(iv) and Titanium (iv) Halides." Journal of The Chemical Society, 1968, London (UK), pp. 69–74.
M.J. Frazer et al., "Reactions of 8–Quinolinol and Covalent Halides. Part III. Zirconium Tetrafluoride and Zirconium, Hafnium and Thorium Tetrachlorides" Journal of The Chemical Society, 1968 London (UK), pp. 2273–2275.
Chemical Abstracts, vol. 102, No. 6, 11 Feb. 1985; Columbus Ohio, US; abstract No. 46311e.

*Primary Examiner*—Mark Nagumo
*Assistant Examiner*—Roberto Rabago
*Attorney, Agent, or Firm*—S. H. Hegedus

[57] ABSTRACT

A catalyst composition for the polymerization of olefins is provided, comprising a bis(hydroxy aromatic nitrogen ligand) transition metal catalyst precursor and an activating cocatalyst.

9 Claims, No Drawings

CATALYST FOR THE PRODUCTION OF OLEFIN POLYMERS

The invention relates to a family of novel catalyst compositions for the production of olefin polymers, such as polymers of ethylene, higher alpha-olefins, dienes, and mixtures thereof.

BACKGROUND

A variety of metallocenes and single site-like catalysts have been developed to prepare olefin polymers. Metallocenes are organometallic coordination complexes containing one or more π-bonded moieties (i.e., cyclopentadienyl groups) in association with a metal atom from Groups IIIB to VIII or the Lanthanide series of the Periodic Table of Elements. Catalyst compositions containing metallocenes and single site-like catalysts are highly useful in the preparation of polyolefins, producing relatively homogeneous copolymers at excellent polymerization rates while allowing one to tailor closely the final properties of the polymer as desired.

U.S. Pat. No. 5,280,000 to Kakugo et al. discloses a catalyst composition for the polymerization of high molecular weight olefins consisting of a transition metal compound of the formula $M(R)_l(OR')_m X_{n-(l+m)}$ (wherein M is a transition metal atom, R and R' are hydrocarbyl groups of 1–20 carbons, X is a halogen, $l \geq 0$, $m > 0$, $n-(l+m) \geq 0$, and n is the valence of the transition metal), an aluminoxane, and optionally an organic compound having at least two hydroxyl groups and optionally an aryl group.

A new single site-like, olefin polymerization catalyst composition is described herein having good polymerization activity and productivity, which is easily and inexpensively prepared. The catalyst composition comprises a bis(hydroxy aromatic nitrogen ligand) transition metal catalyst precursor that is activated with a cocatalyst such as an aluminoxane.

SUMMARY OF THE INVENTION

The invention provides catalyst precursor having a formula selected from the group consisting of:

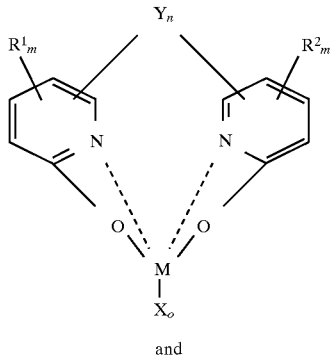

and

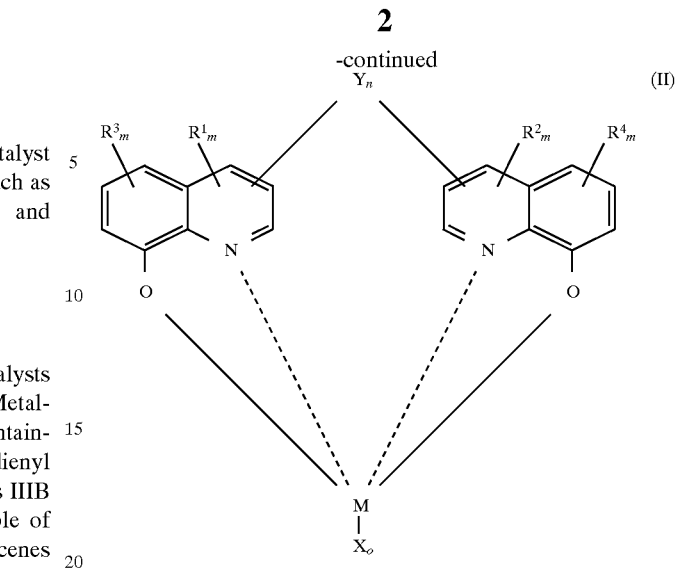

wherein M is a metal selected from the group consisting of Group IIIB to VIII and Lanthanide series elements; each X is a monovalent or bivalent anion; o is 0, 1, 2, or 3 depending on the valence of M; each $R^1$, $R^2$, $R^3$, and $R^4$ is a hydrocarbon group containing 1 to 20 carbon atoms and two or more adjacent $R^1$, $R^2$, $R^3$, or $R^4$ groups may be joined to form an aliphatic, aromatic, or heterocyclic ring; Y is a bivalent bridging group or a bond; each m is independently from 0 to 4; and n is 0 or 1.

The invention also provides a catalyst composition comprising the above catalyst precursor and an activating cocatalyst.

The invention further provides a process for producing an olefin polymer, which comprises contacting an olefin monomer under polymerization conditions with the above catalyst composition, as well as olefin polymers, such as ethylene polymers, produced by this process.

DETAILED DESCRIPTION OF THE INVENTION

The catalyst precursor has one of the following formulas:

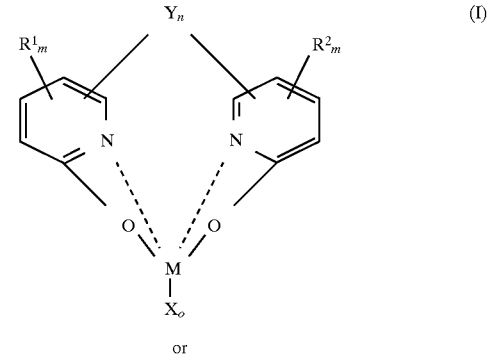

or

-continued

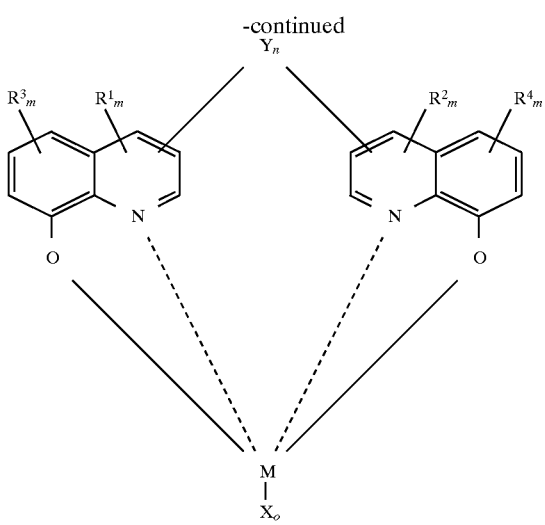

(II)

In the above formula, M is a metal selected from the group consisting of Group IIIB to VIII and Lanthanide series elements, preferably titanium, zirconium, or hafnium, most preferably zirconium. Each X is a monovalent or bivalent anion, preferably selected from the group consisting of hydrogen, aryl, alkyl, alkenyl, alkylaryl, arylalkyl, or hydrocarboxy radicals having 1–20 carbon atoms, —$NR_2$, —OR, or $RCO_2$— wherein R is a hydrocarbon radical having 1 to 20 carbon atoms, and halogens, and o is 0, 1, 2, or 3 depending on the valence of M. More preferably X is a halogen. Each $R^1$, $R^2$, $R^3$, and $R^4$ is a hydrocarbon group containing 1 to 20 carbon atoms and two or more adjacent $R^1$, $R^2$, $R^3$, or $R^4$ groups may be joined to form an aliphatic, aromatic, or heterocyclic ring. Preferably, $R^1$, $R^2$, $R^3$, and $R^4$ are methyl or ethyl groups. Y is a bivalent bridging group or a bond, and is optional. When Y is present, Y is preferably one or more methylene groups. Finally, each m is independently from 0 to 4, preferably 0, and n is 0 or 1.

In a preferred embodiment of the invention, the catalyst precursor has the formula:

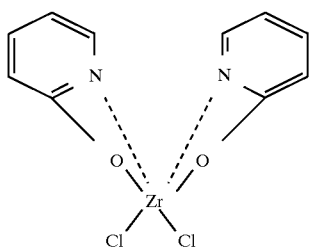

In another preferred embodiment of the invention the catalyst precursor has the formula:

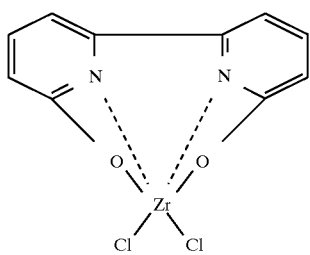

The catalyst precursor may be prepared by any synthesis method, and the method of making the catalyst precursor is not critical to the invention. One useful method of making the catalyst precursor is by reacting a hydroxy aromatic nitrogen compound, which compounds are commercially available, with a metallic deprotonating agent such as an alkyllithium compound in an organic solvent to form the metal salt of the hydroxy aromatic nitrogen compound. The resulting salt may then be reacted with a salt of the desired transition metal, preferably a transition metal halide (i.e., zirconium tetrachloride for a zirconium-containing catalyst precursor) to form the bis(hydroxy aromatic nitrogen ligand) transition metal catalyst precursor. The catalyst precursor may be isolated by methods well known in the art.

The activating cocatalyst is capable of activating the catalyst precursor. Preferably, the activating cocatalyst is one of the following: (a) branched or cyclic oligomeric poly(hydrocarbylaluminum oxide)s which contain repeating units of the general formula —(Al(R*)O)—, where R* is hydrogen, an alkyl radical containing from 1 to about 12 carbon atoms, or an aryl radical such as a substituted or unsubstituted phenyl or naphthyl group; (b) ionic salts of the general formula [$A^+$][$BR^{}_4$—], where $A^+$ is a cationic Lewis or Bronsted acid capable of abstracting an alkyl, halogen, or hydrogen from the metallocene catalysts, B is boron, and R is a substituted aromatic hydrocarbon, preferably a perfluorophenyl radical; (c) boron alkyls of the general formula $BR^{}_3$, where R is as defined above; or mixtures thereof.

Preferably, the activating cocatalyst is a branched or cyclic oligomeric poly(hydrocarbylaluminum oxide) or a boron alkyl. More preferably, the activating cocatalyst is an aluminoxane such as methylaluminoxane (MAO) or modified methylaluminoxane (MMAO), or a boron alkyl.

Aluminoxanes are well known in the art and comprise oligomeric linear alkyl aluminoxanes represented by the formula:

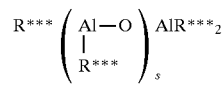

and oligomeric cyclic alkyl aluminoxanes of the formula:

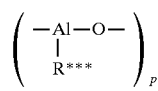

wherein s is 1–40, preferably 10–20; p is 3–40, preferably 3–20; and R*** is an alkyl group containing 1 to 12 carbon atoms, preferably methyl.

Aluminoxanes may be prepared in a variety of ways. Generally, a mixture of linear and cyclic aluminoxanes is obtained in the preparation of aluminoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylaluminoxanes by the reaction of a tetraalkyldialuminoxane containing $C_2$ or higher alkyl groups with an amount of trimethylaluminum that is less than a stoichiometric excess. The synthesis of methylaluminoxanes may also be achieved by the reaction of a trialkyl aluminum compound or a tetraalkyldialuminoxane containing $C_2$ or higher alkyl groups with water to form a polyalkyl aluminoxane, which is then reacted with trimethylaluminum. Further modified methylaluminoxanes, which contain both methyl groups and higher alkyl groups, i.e., isobutyl groups, may be synthesized by the reaction of a polyalkyl aluminoxane containing $C_2$ or higher alkyl groups with trimethylaluminum and then with water as disclosed in, for example, U.S. Pat. No. 5,041,584.

When the activating cocatalyst is a branched or cyclic oligomeric poly(hydrocarbylaluminum oxide), the mole ratio of aluminum atoms contained in the poly (hydrocarbylaluminum oxide) to total metal atoms contained in the catalyst precursor is generally in the range of from about 2:1 to about 100,000:1, preferably in the range of from about 10:1 to about 10,000:1, and most preferably in the range of from about 50:1 to about 2,000:1. When the activating cocatalyst is an ionic salt of the formula $[A^+]$ $[BR^{}_4{-}]$ or a boron alkyl of the formula $BR^{}_3$, the mole ratio of boron atoms contained in the ionic salt or the boron alkyl to total metal atoms contained in the catalyst precursor is generally in the range of from about 0.5:1 to about 10:1, preferably in the range of from about 1:1 to about 5:1.

The catalyst precursor, the activating cocatalyst, or the entire catalyst composition may be impregnated onto a solid, inert support, in liquid form such as a solution or dispersion, spray dried, in the form of a prepolymer, or formed in-situ during polymerization. Particularly preferred among these is a catalyst composition that is spray dried as described in European Patent Application No. 0 668 295 A1 or in liquid form as described in U.S. Pat. No. 5,317,036.

In the case of a supported catalyst composition, the catalyst composition may be impregnated in or deposited on the surface of an inert substrate such as silica, carbon black, polyethylene, polycarbonate porous crosslinked polystyrene, porous crosslinked polypropylene, alumina, thoria, zirconia, or magnesium halide (e.g., magnesium dichloride), such that the catalyst composition is between 0.1 and 90 percent by weight of the total weight of the catalyst composition and the support.

The catalyst composition may be used for the polymerization of olefins by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30° to 130° C., preferably 65° to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,528,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

Conventional adjuvants may be included in the process, provided they do not interfere with the operation of the catalyst composition in forming the desired polyolefin. Hydrogen or a metal or non-metal hydride, e.g., a silyl hydride, may be used as a chain transfer agent in the process. Hydrogen may be used in amounts up to about 10 moles of hydrogen per mole of total monomer feed.

Olefin polymers that may be produced according to the invention include, but are not limited to, ethylene homopolymers, homopolymers of linear or branched higher alpha-olefins containing 3 to about 20 carbon atoms, and interpolymers of ethylene and such higher alpha-olefins, with densities ranging from about 0.86 to about 0.96. Suitable higher alpha-olefins include, for example, propylene, 1-butene, 1-pentene, 1-hexene, 4-methyl-1-pentene, 1-octene, and 3,5,5-trimethyl-1-hexene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

The following examples further illustrate the invention.

EXAMPLES

Glossary

Activity is measured in g polyethylene/mmol metal·hr·100 psi ethylene.

MMAO is a solution of modified methylaluminoxane in hexane, approximately 2.25 molar in aluminum, commercially available from Akzo Chemicals, Inc. (type M).

Hexene incorporation levels in the ethylene copolymers were determined by carbon-13 NMR as follows. An 8% weight/volume concentration was prepared by dissolving an ethylene copolymer in ortho dichlorobenzene (ODCB) in an NMR tube. A closed capillary tube of deuterium oxide was inserted into the NMR tube as a field frequency lock. Data was collected on the Bruker AC 300 at 115° C. using NOE enhanced conditions with a 30° PW and a 5 second repetition time. The number of carbon scans usually varied from 1,000 to 10,000 with the more highly branched samples requiring shorter acquisitions. The area of the peaks was measured along with the area of the total aliphatic region. The areas of carbons contributed by the comonomer were averaged and ratioed to the area of the backbone to give the mole fraction. This number was then converted into branch frequency.

EXAMPLE 1

Preparation of Catalyst Precursor

2-Hydroxypyridine (0.462 g., 4.48 mmole) was dissolved in 25 ml. dry toluene to yield a clear solution. This was reacted with n-butyl lithium (2.80 ml., 1.6M, 4.48 mmole in hexane) and allowed to stir overnight. To this was added drop-wise titanium tetrachloride (0.42 g., 2.24 mmole) via a syringe. This yielded a brown slurry (80 μmole Ti/ml.).

EXAMPLE 2

Preparation of the Catalyst Composition

MMAO (5 ml., 11.25 mmole, 2.25 mmole Al/ml.) was reacted with 0.14 ml. of the catalyst precursor of Example 1 (11.25 μmole Ti) at ambient temperature in a small septum sealed glass ampule to form an active catalyst composition.

EXAMPLE 3

Polymerization of Ethylene

A 1.8 liter, mechanically stirred, pressure reactor was charged with 1 l. of dry, deoxygenated hexanes and pressured to 200 psi, 65° with ethylene. The catalyst composition of Example 2 (0.91 ml., 2 μmole Ti) was injected, through a high-pressure septum into the reactor. Slurry polymerization was carried out at 65°, 275 r.p.m. stirrer speed and 200 psi ethylene for 30 min. and terminated by injection of 1 ml. isopropanol, and reactor venting. The hexanes were allowed to evaporate; the dry solids weighed 8.2 g. This yielded an activity of 4,100.

EXAMPLE 4

Copolymerization of Ethylene-Hexene-1

Example 3 was repeated except that the reactor was also charged with 100 ml. hexene-1. 4.8 g. of polymer were recovered; this was a copolymer of ethylene and hexene-1 containing 5.9 wt. % hexene-1.

EXAMPLE 5

Preparation of Catalyst Precursor

Similar to Example 1, 2-hydroxypyridine (0.380 g., 4.00 mmole) was reacted with n-butyl lithium (22.5 ml., 1.6M in hexane solution) and this further reacted with zirconium tetrachloride (0.499 g., 2.14 mmole) all in 20 ml. hexane solution. The reaction was stirred for 24 hr. to yield a brown slurry.

EXAMPLE 6

Preparation of Catalyst Composition

An aliquot of the catalyst precursor slurry prepared in Example 5 was reacted (as Example 2) with MMAO to yield a catalyst composition solution (Al/Zr~1000).

EXAMPLE 7

Polymerization of Ethylene

Similar to Example 3, the catalyst composition prepared in Example 6 (1.5 ml., 3.0 μmole Zr) was injected into the reactor containing 1 l. hexanes and ethylene (200 psi). Polymerization was continued for 0.5 hr. at 65° and 275 r.p.m. stirrer speed, followed termination with 1 ml. isopropanol. Evaporation of the volatiles yielded 1.8 g. of polyethylene.

We claim:

1. A catalyst precursor having a formula selected from the group consisting of:

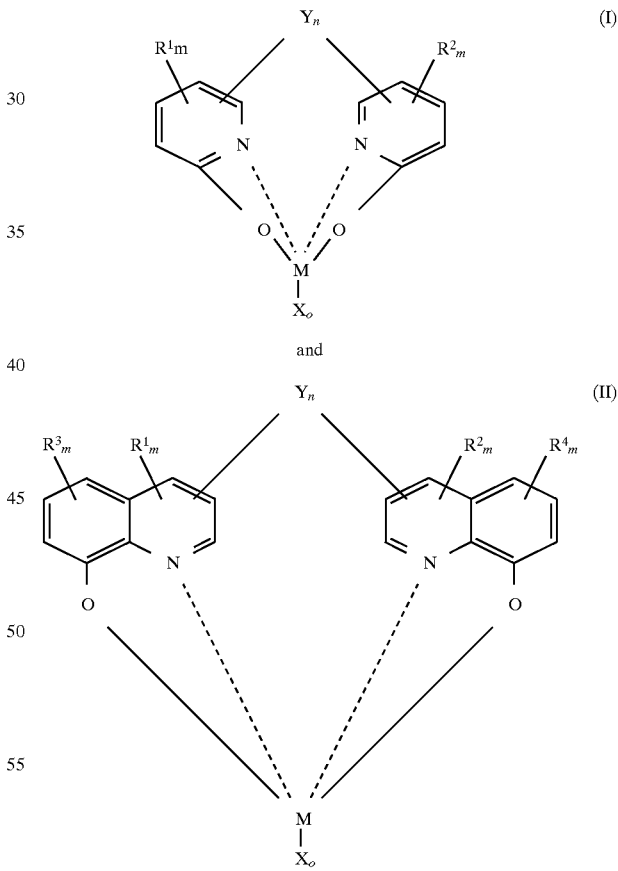

wherein M is a metal selected from the group consisting of Group IIIB to VIII and Lanthanide series elements; each X is selected from the group consisting of hydrogen, aryl, alkyl, alkenyl, alkylaryl, or arylalkyl radicals having 1–20 carbon atoms, —$NR_2$ or $RCO_2$— wherein R is a hydrocarbon radical having 1 to 20 carbon atoms and halogens; o is 0, 1, 2, or 3 depending on the valence of M; each $R^1$, $R^2$, $R^3$, and $R^4$ is a hydrocarbon group containing 1 to 20 carbon atoms and two or more adjacent $R^1$, $R^2$, $R^3$, or $R^4$ groups may be joined to form an aliphatic or aromatic ring; Y is a bivalent bridging group or a bond; each m is independently from 0 to 4; and n is 1.

2. The catalyst precursor of claim 1 having the formula:

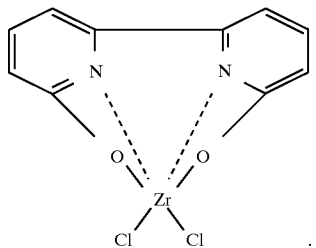

wherein M is a metal selected from the group consisting of Group IIIB to VIII and Lanthanide series elements; each X is a monovalent or bivalent anion; o is 0, 1, 2, or 3 depending on the valence of M; each $R^1$, $R^2$, $R^3$, and $R^4$ is a hydrocarbon group containing 1 to 20 carbon atoms and two or more adjacent $R^1$, $R^2$, $R^3$, or $R^4$ groups may be joined to form an aliphatic, aromatic, or heterocyclic ring; Y is a bivalent bridging group; each m is independently from 0 to 4; and n is 0 or 1; and an activating cocatalyst.

3. A catalyst composition comprising a catalyst precursor having a formula selected from the group consisting of:

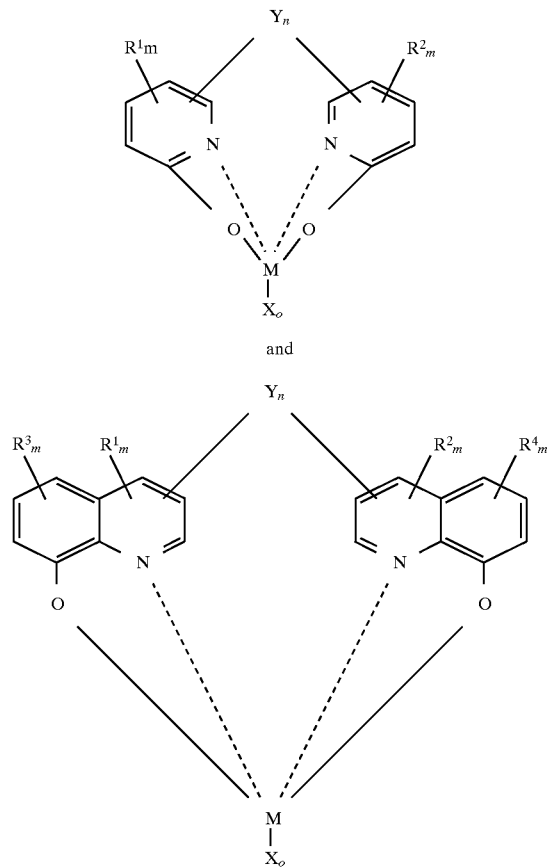

wherein M is a metal selected from the group consisting of Group IIIB to VIII and Lanthanide series elements; each X is selected from the group consisting of hydrogen, aryl, alkyl, alkenyl, alkylaryl, or arylalkyl radicals having 1–20 carbon atoms, —$NR_2$ or $RCO_2$— wherein R is a hydrocarbon radical having 1 to 20 carbon atoms, and halogens; o is 0, 1, 2, or 3 depending on the valence of M; each $R^1$, $R^2$, $R^3$, and $R^4$ is a hydrocarbon group containing 1 to 20 carbon atoms and two or more adjacent $R^1$, $R^2$, $R^3$, or $R^4$ groups may be joined to form an aliphatic or aromatic ring; Y is a bivalent bridging group or a bond; each m is independently from 0 to 4; and n is 1; and an activating cocatalyst.

4. The catalyst composition of claim 3, wherein the catalyst precursor has the formula:

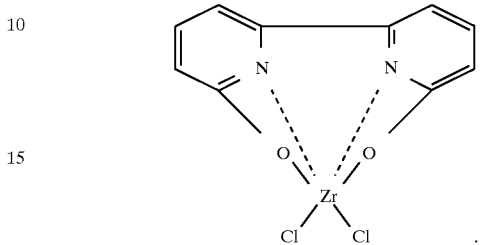

5. A process for producing an olefin polymer, which comprises contacting at least one olefin monomer under polymerization conditions with a catalyst composition comprising: a) a catalyst precursor having a formula selected from the group consisting of:

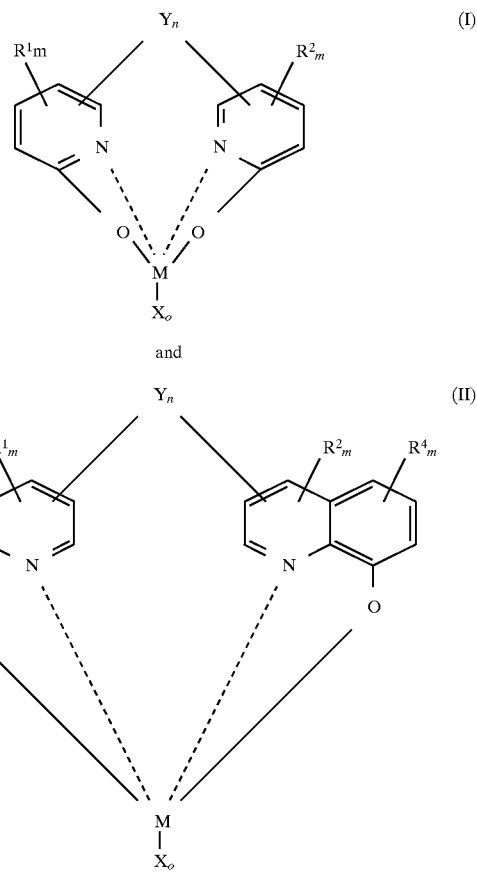

wherein M is a metal selected from the group consisting of Group IIIB to VIII and Lanthanide series elements; each X is a monovalent or bivalent anion; o is 0, 1, 2, or 3 depending on the valence of M; each $R^1$, $R^2$, $R^3$, and $R^4$ is a hydrocarbon group containing 1 to 20 carbon atoms and two or more adjacent $R^1$, $R^2$, $R^3$, or $R^4$ groups may be joined to form an aliphatic or aromatic ring; Y is a bivalent bridging group or a bond; and each m is independently from 0 to 4; and n is 1; and b) an activating cocatalyst.

6. The process of claim 5, wherein the catalyst precursor has the formula:
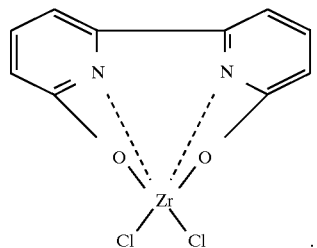
7. The process of claim 5 conducted in the gas phase.
8. The process of claim 5, wherein the catalyst composition is in liquid form.
9. The process of claim 5, wherein the olefin monomer is selected from the group consisting of ethylene, higher alpha olefins, dienes, and mixtures thereof.
* * * * *